United States Patent
Carlberg et al.

Patent Number: 5,428,440
Date of Patent: Jun. 27, 1995

[54] NONINTRUSIVE AIRBORNE IRON BASED PARTICLE DETECTOR

[75] Inventors: Jon R. Carlberg; Eugene H. Barbee; William J. Soules, all of Rochester, N.Y.

[73] Assignee: Eastman Kodak Company, Rochester, N.Y.

[21] Appl. No.: 960,608

[22] Filed: Oct. 13, 1992

[51] Int. Cl.⁶ .......................... G01N 1/40; G01N 1/04
[52] U.S. Cl. ...................................... 356/38; 73/28.01; 73/31.02
[58] Field of Search ................. 356/38, 335, 336, 337, 356/338, 339; 73/28.01, 28.04, 31.01, 31.02, 31.03, 31.07

[56] References Cited

U.S. PATENT DOCUMENTS

| | | |
|---|---|---|
| 3,462,608 | 8/1969 | Weston et al. ............... 250/343 |
| 3,700,330 | 10/1972 | Davis ............................ 356/38 |
| 4,047,814 | 9/1977 | Westcott ........................ 356/38 |
| 4,441,816 | 4/1984 | Hencken et al. ............. 356/335 |

*Primary Examiner*—Vincent P. McGraw
*Attorney, Agent, or Firm*—Carl F. Ruoff

[57] ABSTRACT

The present invention is an apparatus for detecting iron based particulate matter in air/gas streams. The sensor 10 includes a flow through sensor body 11 having an interior surface. A high power magnet 12 for use in attracting airborne iron particulate matter is formed as part 13 of the interior surface of the sensor body. A high contrast photoelectric sensor 14 coupled to a fiber optic bundle 15 is used for detecting changes in the contrast of the magnetic surface.

7 Claims, 1 Drawing Sheet

NONINTRUSIVE AIRBORNE IRON BASED PARTICLE DETECTOR

TECHNICAL FIELD OF THE INVENTION

The present invention relates to an apparatus for detecting iron based particulate matter in an air sample or inert transparent gas.

BACKGROUND OF THE INVENTION

In the manufacture of photographic film and paper, the film and paper are exposed to many different environments as they move through the base manufacturing, sensitizing, and finishing process areas. Occasionally, photographic products can become contaminated with iron particles. Iron being a photographically active material, is a more undesirable contaminant than other nonphotographically active particulate matter. Since iron is used in many machine parts it is inevitable that through normal wear and general part failure iron contamination is going to occur. Iron is also present in indoor and outdoor environmental air, and comes from many sources. Iron can also be brought into buildings on people's feet, product boxes and wheels, product handling trucks and dollies. The much larger (greater than 10 microns) particles of iron do not remain airborne for long once generated. However, it has long been known that much smaller iron particles including submicron sized particles are often generated and made airborne prior to the generation of larger iron particles. These particles can remain airborne for significant periods of time based on their physical size and environmental conditions. Larger particle generation is associated with catastrophic component failure. When this happens there usually will be some level of product waste associated with these contamination events.

There is a need for a way to detect airborne iron particulate matter. The present invention satisfies this need with an apparatus which detects the early warning signs of iron component failure and the presence of high iron contamination in the ambient air.

SUMMARY OF THE INVENTION

The present invention is an apparatus for detecting iron based or other magnetic particulate matter suspended in a gas. The apparatus comprises a sensor body having an interior flow channel with an interior surface, a magnet forming a collection surface on a portion of the interior surface of said sensor body wherein the collection surface is of a high contrast and a photoelectric sensor positioned to receive light reflected from the collection surface. High contrast in the present application refers to any light color, preferably white, which darkens, i.e. reflects less light, as the magnetic particles attach to the surface. When a gas containing suspended iron based particulate matter is passed by the collection surface, the iron based particulate matter is attracted to the magnet thereby changing the contrast of the collection surface which is sensed or detected by the photoelectric sensor.

BRIEF DESCRIPTION OF THE DRAWINGS

The single FIGURE shows the iron based particulate matter detector of the present invention.

For a better understanding of the present invention together with other advantages and capabilities thereof, reference is made to the following description and appended claims in connection with the preceding drawing and description of some aspects of the invention.

DESCRIPTION OF THE PREFERRED EMBODIMENT

Figure 1:
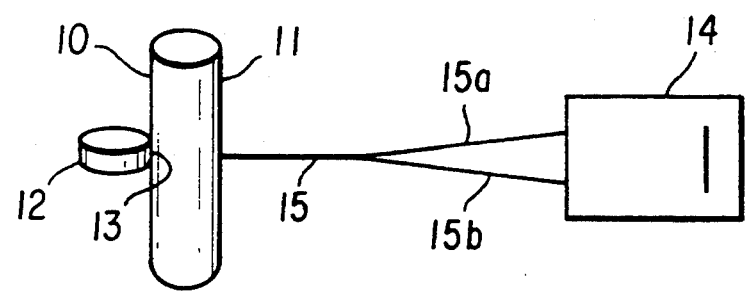

The present invention is a device for sampling iron laden air. The present invention offers the following advantages. The present device samples and detects the presence of airborne iron based particulate matter in a sample area stream. It is a nonintrusive device which can detect airborne iron particles in real time, and can generate an appropriate output signal. The present device does not require visual observation or manual intervention to detect the presence of airborne iron. It can be used to draw an air sample from almost anywhere within a machine or process environment including compressed air/gas streams through the use of sample tubing. Finally, the device is compact and can easily be made part of an existing airborne particle detection system without adversely affecting the operation of the system.

Although the present invention is designed to detect iron based particulate matter in a gaseous stream, it is believed that the detector would work, although not as well, on transparent liquids. Depending on the viscosity and flow rate of the liquid through the device, the iron particles may not be as readily attracted to the magnetic surface. Therefore, redesigning the shape and size of the magnetic surface would be required in order to detect magnetic particles in a liquid.

The present invention utilizes a nonintrusive flow through body which allows for the free passage of air or other inert transparent gaseous media. The sensor is unique in that in most environments, it detects only iron based particles due to its construction and mode of operation. It does not need to be manually investigated unless the sensor head needs cleaning after, for example, an iron contamination event has occurred.

Shown in the FIGURE is a schematic of the sensor of the present invention. The sensor 10 is made up of three basic components. The first component is the flow through sensor body 11 made of a conductive material which is compatible with the environmental air/gas stream being sampled. A preferred material is 316 stainless steel. The sensor body 11 is also preferably cylindrical and has a fine microfinish interior wall surface. A high power magnet 12 is used for attracting airborne iron particulate matter. The face 13 of the magnet 12 is treated or covered with a bright white surface material for high contrast. High contrast in the present application refers to any surface shading or light color, preferably white, which darkens and therefore reflects less light as the magnetic particles adhere to the surface. This can include a thin coating of epoxy paint, a dip spray coating of Teflon or the application of vinyl tape. The final element is a high contrast photoelectric sensor 14 coupled to a fiber optic bundle 15. The fiber optic bundle 15 must include a light emitter 15a and a detector 15b. The fiber optic can either be bifurcated i.e., combining both functions into a single fiber optic bundle, or separate bundles can be used for the emitter 15a and detector 15b.

Light from the photoemitter 15a is shown onto the bright white surface 13 positioned before the magnet 12. The amount of light reflected back to the detector 14 will decrease as iron begins to load the magnetic surface 13. Thus, a simple measure of airborne iron can be extracted as a decrease in surface contrast measured by the detector.

The output of the photodetector emitter 14 can be used to trigger an alarm (not shown) through a computer (not shown) or other means once the contrast of the surface changes by a predetermined amount. Flow through the sensor can be generated from a stand-alone vacuum pump or the sensor can be tied into an existing flow system such as an airborne particle monitoring system. With the use of existing piping, the sensor body can be sized appropriately so as not to cause a restriction or contraction within an existing air sampling system.

Air/gas samples of either a defined volume or continuous real time are run past the magnetic surface. It is preferred that the magnetic strength of the surface be a minimum of 25 MGOe on up. The device of the present invention used a neodymium iron boron (NdFeB) magnet manufactured from ½" rod having a strength of approximately 35 MGOe. Any entrained airborne iron based particles will be preferentially attracted to the magnetic surface. The magnet used can be either of the rare earth type magnets or electromagnets. The magnetic surface exposed to the sample air/gas stream is given a bright white surface treatment. This is done to create a high contrast ratio for any iron particles which appear as dark spots when collected on the white magnetic surface. This collection surface can be made of a wide range of materials. The surface treatment can be made tacky or smooth and glossy depending upon the application. The only requirement of the present invention is that the surface treatment not attenuate an appreciable amount of the magnetic force. The white magnetic surface is continually monitored through the use of a photoelectric sensor which may be either directly connected to the sensor body, or remotely monitored through the use of a single bifurcated fiber optic light guide or a two fiber optic light guide, one for the light emitter source and the other for the light detector. In tests on the present invention it was found that the bifurcated fiber optic worked well and was preferred in the sensor body constructed for the test due to space limitations.

The test included the collection of random room air samples, and the seeding of the samples with AC air filter dust which contained iron particles. The results showed the sensor's ability to separate the iron particles from the other components of the test dust, thus giving positive readings on output from the photodetector unit. The positive reading was determined by a change in contrast from the initial reading as the amount of dust increased.

A high contrast photodetector available from Tri-Tronics Inc., can detect minute changes in reflected light returned back to the photodetector from the monitored white surface. As the surface attracts iron particles it darkens resulting in less light reflected back to the detector. Sample air is drawn past the sensor such that the flow is turbulent. This means that the fluid sample flow rate is commensurate with a Reynolds number of at least 2200. This is done to minimize settling of other non-iron particles onto the magnetic collection surface and fiber optic surface. However, the flow through the sensor body should not be so great as to prevent a significant portion of the airborne iron particles from being properly captured on the magnetic surface.

The magnetic surface and the fiber optic light guide should be milled to match the interior contours of the sensor body, or positioned such that they are minimally intrusive to the flowing air/gas stream. This is done to prevent or minimize unwanted settling of non-iron particles on the magnetic and fiber optic surfaces. The sensor body can be constructed of any smooth wall interior conductive material. Polished 316 grade stainless steel was used for the test for the present invention and is considered a good choice for most applications. The results to date show a linear drop in reflected light from the target surface as measured by a change in contrast. The present tests included a ½ inch diameter flow channel with a flow rate of about 2–3 cubic feet/min. The sensor body should be kept electrically grounded. This is done to minimize unwanted nonmagnetic particle settling in the sensor body housing. In operation, the magnetic surface and fiber optic light guide are on the same plane when using bifurcated light guides, and at an angle of best reflection for a two fiber optic bundle construction. The light from the fiber optic must be properly focused on the entire magnetic surface. The optimum operational plane is with the sensor body positioned such that the flow through the sensor is drawn parallel to gravity.

The magnetic surface darkens with iron loading and the photo detector senses the changes in contrast over time. Either an analog or digital output from the sensor for changes in operational state can be used for the detection of airborne based iron particles through several means.

While there has been shown and described what are at present considered the preferred embodiments of the invention, it will be obvious to those skilled in the art that various changes, alterations and modifications may be made therein without departing from the scope of the invention as defined by the appended claims.

What is claimed:

1. An apparatus for detecting magnetic particular matter suspended in a gas comprising:
   a sensor body having a flow channel with an interior surface;
   a magnet forming a collection surface on a portion of the interior surface of said sensor body wherein the collection surface is of a contrast;
   means positioned to shine light on the collection surface; and
   a photoelectric sensor positioned to receive light reflected from the collection surface
   wherein when the gas containing suspended magnetic particulate matter is passed by the interior surface, the magnetic particulate matter is attracted to the magnet thereby changing the contrast of the collection surface which is detected by the photoelectric sensor.

2. The apparatus according to claim 1 wherein the magnet is a rare earth magnet.

3. The apparatus according to claim 1 wherein the magnet is an electromagnet.

4. The apparatus according to claim 1 wherein the magnet has a strength of approximately 25 MGOe or greater.

5. The apparatus according to claim 1 wherein the sensor body comprises a conductive material.

6. The apparatus according to claim 1 wherein the flow of gas past the collection surface is turbulent.

7. The apparatus according to claim 1 wherein the photodetector sensor and means positioned to shine light comprise a bifurcated fiber optic light guide.

* * * * *